United States Patent [19]
Essig et al.

[11] Patent Number: 5,304,124
[45] Date of Patent: Apr. 19, 1994

[54] MYOMA REMOVAL TECHNIQUE

[76] Inventors: Mitchell N. Essig, 227 High Brook Ct., Pelham, N.Y. 10803; Peter J. Wilk, 185 W. End Ave., New York, N.Y. 10023

[21] Appl. No.: 72,769

[22] Filed: Jun. 7, 1993

[51] Int. Cl.$^5$ ............... A61M 31/00; A61B 17/20; A61B 17/36
[52] U.S. Cl. ........................ 604/55; 604/22; 606/29
[58] Field of Search ............ 604/49, 51, 54, 55, 604/22, 113, 114, 117, 158; 606/27-31, 107, 170

[56] References Cited

U.S. PATENT DOCUMENTS

| | | | |
|---|---|---|---|
| 3,982,542 | 9/1976 | Ford et al. | 606/29 |
| 4,349,033 | 9/1982 | Eden | 128/660 |
| 4,807,595 | 2/1989 | Hiltebrandt | 128/4 |
| 4,830,002 | 5/1989 | Semm | 606/207 |
| 4,869,248 | 9/1989 | Narula | 606/29 |
| 4,936,281 | 6/1990 | Stasz | 128/660.03 |
| 4,949,718 | 8/1990 | Neuwirth et al. | 607/105 |
| 5,027,792 | 7/1991 | Meyer | 128/6 |
| 5,158,561 | 10/1992 | Rydell et al. | 606/113 |
| 5,176,677 | 1/1993 | Wuchinich | 606/46 |
| 5,195,956 | 3/1993 | Stockmeier | 604/22 |

FOREIGN PATENT DOCUMENTS 3545176  7/1987  Fed. Rep. of Germany ........ 604/22

Primary Examiner—John D. Yasko
Assistant Examiner—Adam J. Cermak
Attorney, Agent, or Firm—R. Neil Sudol; Henry D. Coleman

[57] ABSTRACT

In a method for removing a myoma, a distal end portion of a tubular member is inserted through laparoscopic trocar sleeve disposed in the patient's abdomen. The distal end portion of the tubular member is inserted into the myoma tissues to form a core thereof inside the tubular member. The myoma core is fragmented via an energizable laparoscopic instrument and the fragments are aspirated from the tubular coring member. The tubular member may be provided along a distal edge with a cauterizing element for facilitating the insertion of the distal end portion of the tubular member into the myoma.

16 Claims, 2 Drawing Sheets

MYOMA REMOVAL TECHNIQUE

BACKGROUND OF THE INVENTION

This invention relates to a laparoscopic surgical procedure for use in removing a myoma. This invention also relates to an associated surgical assembly.

A myoma is a fibroid mass of tumorous uterine tissue, solid and benign. A myoma can be as large as a baby's head and can squeeze the Fallopian tubes or the uterine cavity, preventing pregnancy. Because a myoma is massive and incompressible, it poses substantial problems in removal from the abdominal cavity via conventional laparoscopic procedures. Unlike a gall bladder, for example, a myoma frequently cannot be simply pulled through a laparoscopic trocar perforation. Moreover, chopping a myoma into smaller tissue parts can cause a significant amount of bleeding.

One technique is known for the laparoscopic removal of myoma tissues. That technique includes the manual insertion of a tubular member into the myoma, thereby forming a myoma core inside the tubular member. Subsequently, laparoscopic graspers are inserted into the tubular member to pull the myoma tissues therefrom.

This technique is difficult and requires a lot of energy.

OBJECTS OF THE INVENTION

An object of the present invention is to provide a method for use in the laparoscopic removal of myoma tissues.

Another object of the present invention is to provide such a method which is relatively easy and quick.

A further object of the present invention is to provide an associated instrument assembly for use in extracting a myoma via laparoscopic procedures.

Yet another object of the present invention is to provide such an instrument assembly and related method wherein the loss of blood is reduced, if not minimized, over known procedures.

These and other objects of the present invention will be apparent from the drawings and detailed descriptions herein.

SUMMARY OF THE INVENTION

A method for removing a myoma comprises, in accordance with the present invention, the steps of (a) providing a laparoscopic trocar sleeve and a tubular member provided along a distal edge with a cauterizing element, (b) lifting a woman's abdominal wall, (c) disposing the trocar sleeve in the lifted abdominal wall, (d) inserting the tubular member through the trocar sleeve so that the distal end contacts a myoma in the woman's uterus, (e) moving the tubular member further in a distal direction and into the myoma upon contact of the distal edge with the myoma, thereby forming a core of myoma tissues inside the tubular member, (f) energizing the cauterizing element during the step of moving, to enable the cauterizing element to cut through the myoma, (g) terminating the distal motion of the tubular member and the energizing of the cauterizing element upon attaining a predetermined depth in the myoma, and (h) removing the core of myoma tissues in a proximal direction through the tubular member and the trocar sleeve upon termination of distal movement of the tubular member.

According to another feature of the present invention, the removal of the myoma core is implemented by providing a laparoscopic morselating instrument and a laparoscopic suction device, inserting the morselating instrument through the tubular member to the myoma core inside the tubular member, actuating the morselating instrument to fragment the core, and activating the suction device in the tubular member to aspirate myoma core fragments produced by the use of the morselating instrument.

According to a more specific feature of the present invention, the morselating instrument is a rotary device having a cutting edge at a distal end. Actuation of the morselating instrument includes the step of rotating the rotary device. Alternatively, the morselating instrument includes an optical fiber. In that case, the step of actuating the actuation of the morselating instrument includes the step of transmitting a laser beam through the optical fiber.

According to an additional feature of the present invention, the suction device is inserted simultaneously with the morselating instrument into the tubular member. The suction then takes place substantially simultaneously with the fragmentation or morselating.

According to a further feature of the present invention, the tubular member is provided along an outer surface with a distance scale. The method then further comprises the step of visually monitoring the scale during the motion of the tubular member into the myoma to ascertain attainment of the predetermined depth.

The cauterizing element may be a Bovie type component, the step of energizing including the step of transmitting electromagnetic radiation through organic tissues of the woman.

According to yet another feature of the present invention, the method further comprises the steps, executed upon termination of distal movement of the tubular member, of shifting the cauterizing element in a direction substantially transverse to the tubular member and energizing the cauterizing element during the step of shifting, thereby serving to sever the core from the uterus.

A laparoscopic instrument assembly comprises, in accordance with the present invention, a tubular member insertable through a laparoscopic trocar sleeve, a morselating instrument slidably inserted into the tubular member, and a suction device also slidably inserted into the tubular member.

Pursuant to another feature of the present invention, the tubular member is provided along an outer surface with a distance scale. The scale enables the attainment of uniformity where multiple coring is required to remove a myoma.

Preferably, a motor is operatively connected to the morselating instrument for actuating the instrument. For example, the motor rotates a drill or whip.

BRIEF DESCRIPTION OF THE DRAWING

Figure 1:
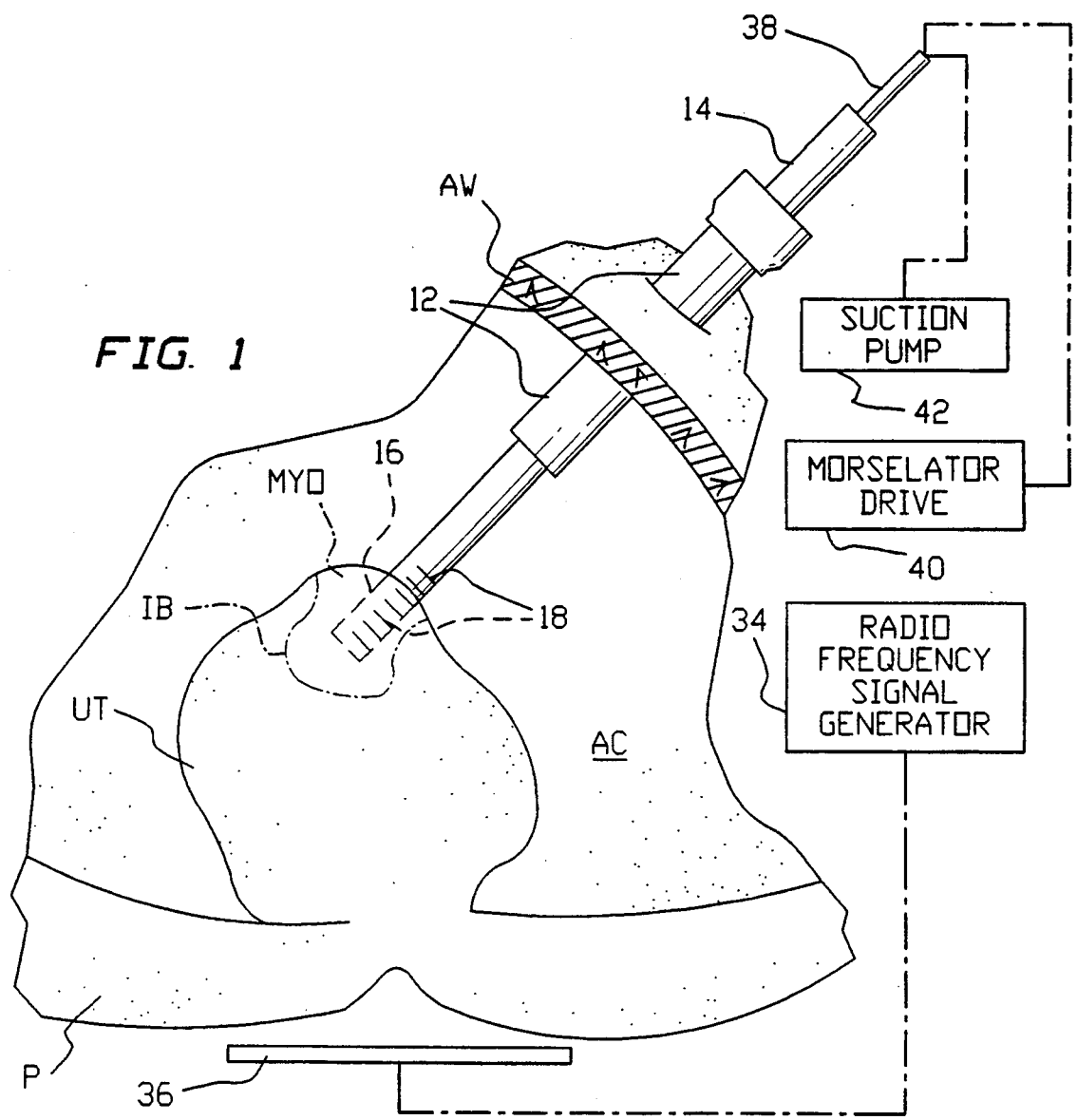
FIG. 1 is partially a schematic side elevational view and partially a block diagram of a laparoscopic instrument assembly in accordance with the present invention, during a stage of a myoma removal procedure in accordance with the invention.

In a laparoscopic procedure for removing a myoma MYO from a patient's uterus UT, illustrated partially in FIG. 1, a laparoscopic trocar sleeve 12 is disposed in an abdominal wall AW which has been distended, for example, under the application of gaseous pressure inside an abdominal or peritoneal cavity AC. A tubular member 14 is inserted through trocar sleeve 12 so that a distal end portion 16 penetrates myoma MYO. Distal end portion 16 is provided with scale markings 18 which enable a surgeon to gauge the extend of penetration of tubular distal end portion 16 into uterine tissues.

Figure 2:
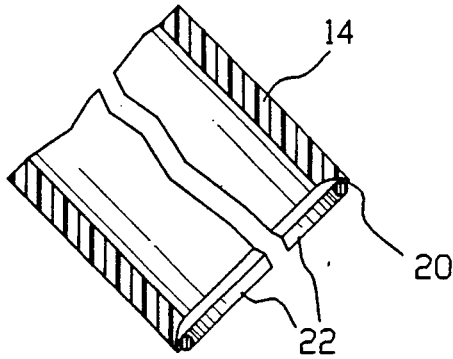
FIG. 2 is a partial schematic cross-sectional view of a portion of the laparoscopic instrument assembly of FIG. 1.
Figure 3:
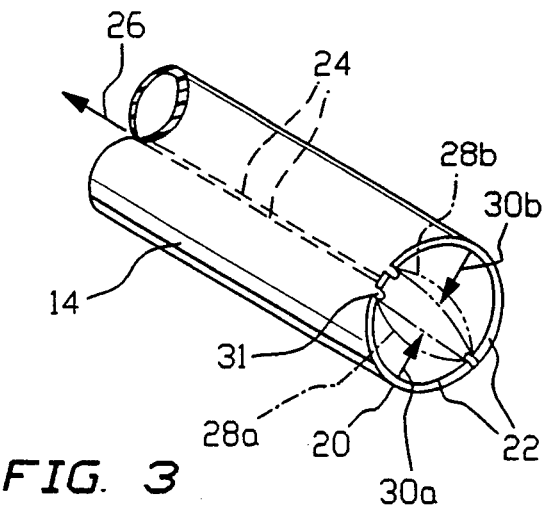
FIG. 3 is a partial schematic perspective view also of a portion of the laparoscopic instrument assembly of FIG. 1.

As illustrated in FIGS. 2 and 3, tubular member 14 is provided along a distal edge 20 with a circular cauterizing wire loop 22. Wire loop 22 is spring biased to assume a circular configuration as illustrated in solid lines in FIG. 3. During a distally directed insertion stroke of trocar sleeve 12, wire loop 22 is energized to cut and cauterize uterine tissues. Upon attainment of the inner boundary IB of myoma mass MYO by the distal edge 20 of tubular member 14, as determinable by monitoring scale markings 18, a tensile force is applied to longitudinally extending wire segments 24, as indicated by arrow 26. The pulling of wire segments 24 in the proximal direction causes loop 22 to deform into a pair of loop sections 28a and 28b moving inwardly, as indicated by arrows 30a and 30b. During that inward motion of loop sections 28a and 28b, loop 22 continues to cut and cauterize uterine tissues, thereby severing a cylindrical core of myoma tissues which is lodged inside tubular member 14. Loop 22 is secured to tubular member 14 along edge 20 by a plurality of hooks or eyelets 31.

Figure 4:
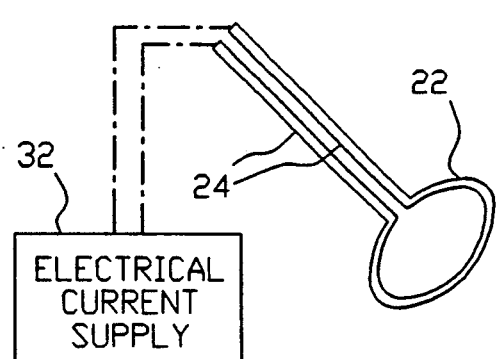
FIG. 4 is partially a partial schematic perspective view and partially a block diagram, depicting a modified version of the laparoscopic tissue removal assembly of FIG. 1.

As illustrated in FIG. 4, loop 22 may be energized by a conventional electrical current supply 32 connected to loop 22 via wire segments 24. Alternatively, as depicted in FIG. 1, a radio-frequency generator 34 is connected to a radiator or antenna 36 disposed in juxtaposition to the patient P. Radio-frequency electromagnetic waves are emitted from radiator 36 and cause a temperature elevation of wire loop 22. In the event that the field produced by radiator 36 is magnetic, current arises in loop 22 owing to magnetic flux. The current produces heat owing to resistance of the wire. Alternatively, a Bovie type energization may be implemented to enable the cutting and/or cauterization of tissues by wire loop 22.

As further illustrated in FIG. 1, a laparoscopic morselator instrument 38 is inserted into tubular member 14 to fragment the myoma core disposed inside the tubular member upon the insertion thereof into myoma mass MYO. Morselator instrument 38 is operatively connected to a drive 40 for actuating the morselator and to a suction pump or other vacuum source 42 for extracting tissue fragments during operation of the morselator instrument upon insertion of distal end portion 16 of tubular member 14 into myoma MYO.

Figure 5:
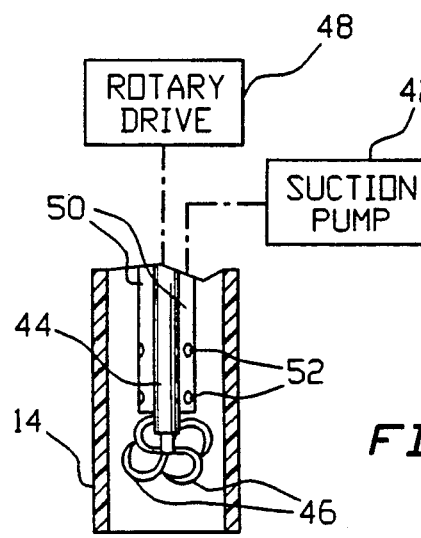
FIG. 5 is partially a schematic cross-sectional view and partially a block diagram of another embodiment of a laparoscopic tissue removal assembly for use in a method in accordance with the present invention.

In a particular embodiment of morselator instrument 38, illustrated in FIG. 5, a rotatable shaft 44 carries a plurality of curved blades 46 at a distal end, morselator drive 40 taking the form of a rotary drive 48. Suction pump or source 42 is connected to a pair of tubes 50 provided with openings 52 at their distal ends. Upon insertion of the morselator instrument of FIG. 5 into tubular member 14, the rotation of shaft 44 causes blades 46 to chop myoma tissues inside tubular member 14 into fragments for aspiration by source 42 via tubes 50.

Figure 6:
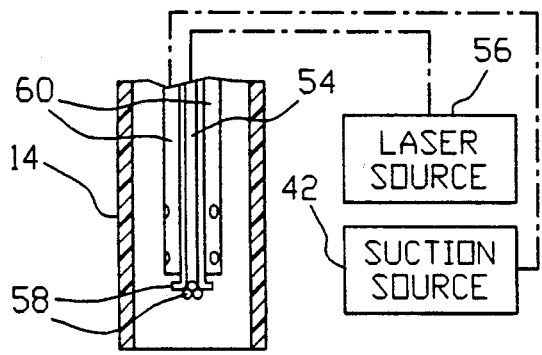
FIG. 6 is partially a schematic cross-sectional view and partially a block diagram, indicating an additional embodiment of a laparoscopic tissue removal assembly for use in a method in accordance with the present invention.

In another particular embodiment of morselator instrument 38, illustrated in FIG. 6, a fiber optic bundle 54 is connected at a proximal end to a pulsed laser source 56 and is provided at a distal end with a plurality of radially bent terminal parts 58. Suction tubes 60 are connected to suction pump or source 42. Upon insertion of the morselator instrument of FIG. 6 into tubular member 14, laser radiation transmitted through optical fiber bundle 54 cuts the myoma tissues inside the tubular member, whereupon fragments are aspirated via tubes 60 and suction source 42.

Figure 7:
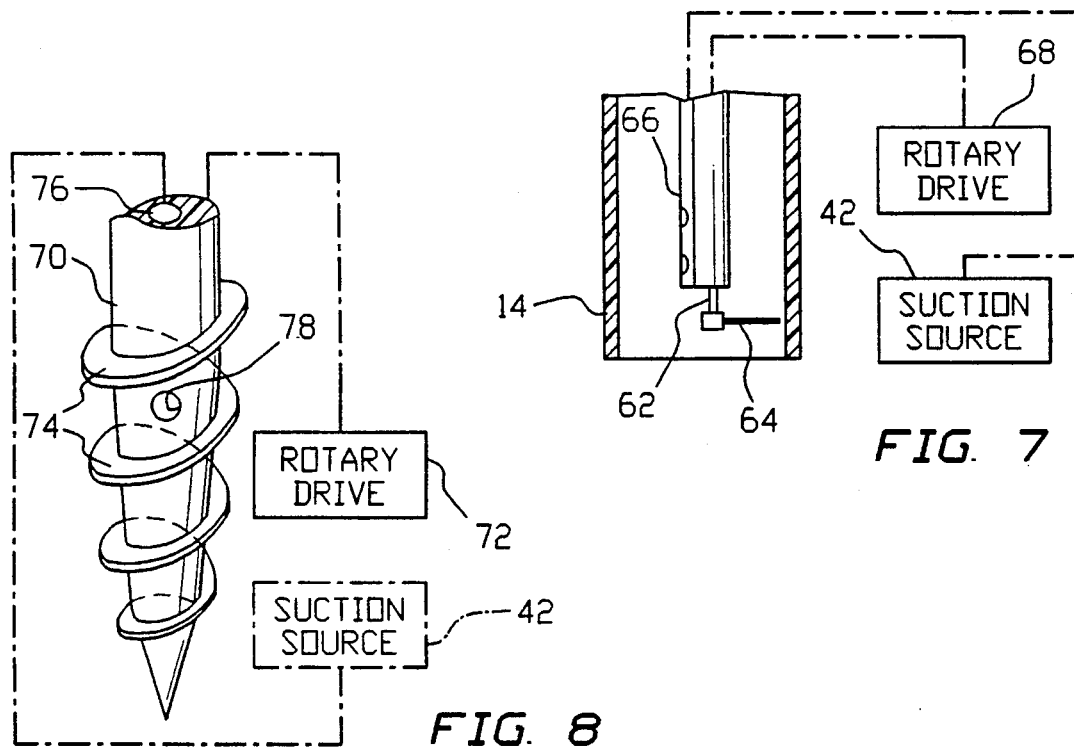
FIG. 7 is partially a schematic cross-sectional view and partially a block diagram, showing yet another embodiment of a laparoscopic tissue removal assembly for use in a method in accordance with the present invention.

As depicted in FIG. 7, yet another laparoscopic morselator for use in executing the method discussed hereinabove with reference to FIG. 1 comprises a rotatable shaft 62 provided at a free end with a flexible tensile element 64 which whips through myoma tissues to reduce them to fragments aspiratable through a tube 66 under the action of suction pump or source 42. Shaft 62 is connected at a proximal end to a rotary drive 68.

Figure 8:
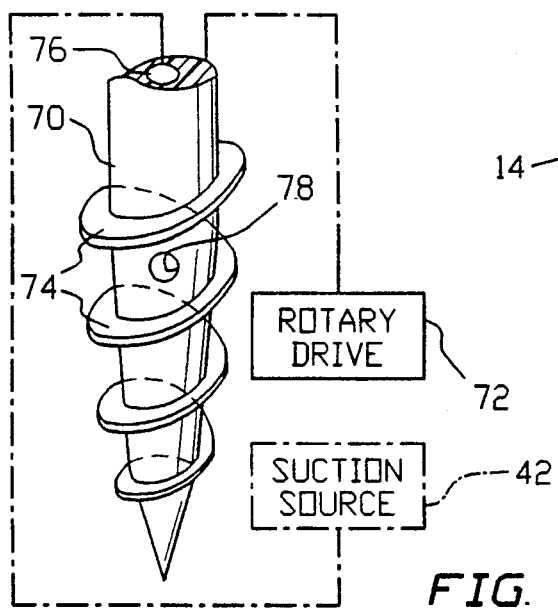
FIG. 8 is partially a schematic cross-sectional view and partially a block diagram, illustrating yet a further embodiment of a laparoscopic tissue removal assembly for use in a method in accordance with the present invention.

As shown in FIG. 8, an alternative laparoscopic morselator for use in removing a core of myoma tissues from tubular member 14 includes a shaft 70 drivingly connected to a motor or other rotary drive 72 and provided with a screw thread 74 for cutting myoma tissues in an endless strip. In the event that the tissues shred, shaft 70 is provided with a channel 76 with at least one suction opening 78.

It is to be noted that the morselating and suction procedures of the invention may be implemented with the cauterization. In that event, the distal edge 20 of tubular member 14 is sufficiently sharp to penetrate myoma MYO under the application of a distally directed force.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A method for removing a myoma, comprising the steps of:
   providing a laparoscopic trocar sleeve and a tubular member provided along a distal edge with a cauterizing element;
   lifting a woman's abdominal wall;
   disposing said trocar sleeve in the lifted abdominal wall;
   inserting said tubular member through said trocar sleeve so that said distal end contacts a myoma in the woman's uterus;
   upon contact of said distal edge with said myoma, moving said tubular member further in a distal direction and into said myoma, thereby forming a core of myoma tissues inside said tubular member;
   during said step of moving, energizing said cauterizing element to enable said cauterizing element to cut through said myoma;
   upon attaining a predetermined depth in said myoma, terminating said steps of moving and energizing; and
   upon termination of distal movement of said tubular member, removing said core of myoma tissues in a proximal direction through said tubular member and said trocar sleeve.

2. The method defined in claim 1 wherein said step of removing includes the steps of:
   providing a laparoscopic morselating instrument and a laparoscopic suction device;
   inserting said morselating instrument through said tubular member to the myoma core inside said tubular member;
   actuating said morselating instrument to fragment said core; and
   activating said suction device in said tubular member to aspirate myoma core fragments produced by said step of actuating.

3. The method defined in claim 2 wherein said morselating instrument is a rotary device having a cutting edge at a distal end, said step of actuating including the step of rotating said rotary device.

4. The method defined in claim 2 wherein said morselating instrument includes an optical fiber, said step of actuating including the step of transmitting a laser beam through said optical fiber.

5. The method defined in claim 2 wherein said suction device is inserted simultaneously with said morselating instrument into said tubular member, said step of activating taking place substantially during said step of actuating.

6. The method defined in claim 1 wherein said tubular member is provided along an outer surface with a distance scale, further comprising the step of visually monitoring said scale during said step of moving to ascertain attainment of said predetermined depth.

7. The method defined in claim 1 wherein said cauterizing element is a Bovie type element, said step of energizing including the step of transmitting electromagnetic radiation through organic tissues of the woman.

8. The method defined in claim 1, further comprising the steps, executed upon termination of distal movement of said tubular member, of shifting said cauterizing element in a direction substantially transverse to said tubular member and energizing said cauterizing element during said step of shifting, thereby serving to sever said core from the uterus.

9. A method for removing a myoma, comprising the steps of:
   providing a laparoscopic trocar sleeve, a tubular member, a laparoscopic morselating instrument, and a laparoscopic suction device;
   lifting a woman's abdominal wall;
   disposing said trocar sleeve in the lifted abdominal wall;
   inserting said tubular member through said trocar sleeve so that said distal end contacts a myoma in the woman's uterus;
   upon contact of said distal edge with said myoma, moving said tubular member further in a distal direction and into said myoma, thereby forming a core of myoma tissues inside said tubular member;
   terminating said step of moving upon attaining a predetermined depth in said myoma;
   upon termination of distal movement of said tubular member, inserting said morselating instrument through said tubular member to the myoma core inside said tubular member;
   actuating said morselating instrument to cut said core into fragments; and
   activating said suction device in said tubular member to aspirate said fragments out of said tubular member.

10. The method defined in claim 9 wherein said morselating instrument is a rotary device having a cutting edge at a distal end, said step of actuating including the step of rotating said rotary device.

11. The method defined in claim 9 wherein said morselating instrument includes an optical fiber, said step of actuating including the step of transmitting a laser beam through said optical fiber.

12. The method defined in claim 9 wherein said suction device is inserted simultaneously with said morselating instrument into said tubular member, said step of activating taking place substantially during said step of actuating.

13. The method defined in claim 9 wherein said tubular member is provided along an outer surface with a distance scale, further comprising the step of visually monitoring said scale during said step of moving to ascertain attainment of said predetermined depth.

14. The method defined in claim 9 wherein said tubular member is provided along a distal edge with a cauterizing element, also comprising the step of energizing said cauterizing element, during said step of moving, to enable said cauterizing element to cut through said myoma.

15. The method defined in claim 14 wherein said cauterizing element is a Bovie type element, said step of energizing including the step of transmitting electromagnetic radiation through organic tissues of the woman.

16. The method defined in claim 14, further comprising the steps, executed upon termination of distal movement of said tubular member, of shifting said cauterizing element in a direction substantially transverse to said tubular member and energizing said cauterizing element during said step of shifting, thereby serving to sever said core from the uterus.

* * * * *

UNITED STATES PATENT AND TRADEMARK OFFICE
CERTIFICATE OF CORRECTION

PATENT NO. : 5,304,124
DATED : April 19, 1994
INVENTOR(S) : Mitchell N. Essig and Peter J. Wilk It is certified that error appears in the above-indentified patent and that said Letters Patent is hereby corrected as shown below:

Column 3, line 25, change "BRIEF" to --DETAILED--; line 35, change "extend" to --extent--.

Signed and Sealed this

Seventh Day of February, 1995

Attest:

BRUCE LEHMAN

*Attesting Officer*   *Commissioner of Patents and Trademarks*